(12) United States Patent
Huang et al.

(10) Patent No.: US 10,575,768 B2
(45) Date of Patent: Mar. 3, 2020

(54) MULTI-FUNCTIONAL SPECIMEN COLLECTOR

(71) Applicants: Shih-Hua Huang, Taipei (TW);
Fang-Tsern Liu, Taipei (TW);
Tzu-Chun Liu, Taipei (TW)

(72) Inventors: Shih-Hua Huang, Taipei (TW);
Fang-Tsern Liu, Taipei (TW);
Tzu-Chun Liu, Taipei (TW)

(73) Assignees: Shih-Hua Huang, Taipei (TW);
Fang-Tsern Liu, Taipei (TW)

( * ) Notice: Subject to any disclaimer, the term of this patent is extended or adjusted under 35 U.S.C. 154(b) by 341 days.

(21) Appl. No.: 15/687,223

(22) Filed: Aug. 25, 2017

(65) Prior Publication Data

US 2018/0064383 A1    Mar. 8, 2018

(30) Foreign Application Priority Data

Sep. 6, 2016  (TW) .............................. 105128803 A

(51) Int. Cl.

| A61B 5/153 | (2006.01) |
|---|---|
| A61B 5/15 | (2006.01) |
| A61M 5/178 | (2006.01) |
| B01L 3/00 | (2006.01) |

(52) U.S. Cl.
CPC .......... *A61B 5/153* (2013.01); *A61B 5/15003* (2013.01); *A61B 5/150236* (2013.01); *A61B 5/150244* (2013.01); *A61B 5/150351* (2013.01); *A61M 5/178* (2013.01); *B01L 3/5021* (2013.01); *A61B 5/150389* (2013.01); *A61B 5/150503* (2013.01); *A61B 5/150824* (2013.01); *B01L 2200/026* (2013.01); *B01L 2200/028* (2013.01); *B01L 2200/0689* (2013.01); *B01L 2300/028* (2013.01); *B01L 2400/0409* (2013.01); *B01L 2400/0478* (2013.01)

(58) Field of Classification Search
CPC ................ A61B 5/15; A61B 5/150206; A61B 5/150236; A61B 5/150244; A61B 5/150351; A61B 5/150343; A61B 5/150763; A61B 5/153
See application file for complete search history.

(56) References Cited

U.S. PATENT DOCUMENTS

| 3,921,630 | A | * | 11/1975 | McPhee | .................... | A61J 1/05 604/530 |
|---|---|---|---|---|---|---|
| 3,937,211 | A | * | 2/1976 | Merten | ............ | A61B 5/150908 600/578 |
| 6,264,620 | B1 | * | 7/2001 | Shieh | ................. | A61B 5/15003 600/576 |

* cited by examiner

*Primary Examiner* — Carrie R Dorna

(57) ABSTRACT

A multi-functional specimen collector comprises a barrel, a shaft body disposed in the barrel, a piston disposed in the barrel and connected to the shaft body, a first seal cap connected to an end of the barrel, and a second seal cap for connecting to the piston after the shaft body is removed. An interior at the end of the barrel is disposed a stopper for restricting a moving range of the piston inside the barrel to prevent the piston from being pulled out of the barrel. The outer diameter of the stopper and the inner diameter of the barrel are designed to closely fit each other. The inner diameter of the stopper might be smaller than the outer diameter of the piston, and the inner diameter of the stopper might be larger than the largest outer diameter of the shaft body.

5 Claims, 6 Drawing Sheets

MULTI-FUNCTIONAL SPECIMEN COLLECTOR

CROSS-REFERENCE TO RELATED APPLICATIONS

The application claims priority from Taiwan Patent Application No. 105128803 filed on Sep. 6, 2016, the disclosure of which is incorporated herein by reference.

BACKGROUND OF THE INVENTION

1. Field of the Invention

The present invention relates to a multi-functional specimen collector and particularly to a multi-functional specimen collector which, in substitution for a test tube, provides the functions of specimen collection and storage and which may be centrifugally treated and is spillover proof.

2. Description of Related Art

Conventional injection syringes are usually used to collect specimens (e.g. blood). A conventional injection syringe primarily includes a barrel A, a needle B disposed at a front end of the barrel A, a piston C disposed inside the barrel A, and a push shaft D connected to the piston C and located at a rear segment of the barrel A (not shown in the figures). When the injection syringe is used, the needle B is inserted into a human blood vessel and the push shaft D is pulled for forming a negative pressure inside the barrel A to extract a human blood specimen and store it in the barrel A. After the specimen is extracted, the needle B is inserted into a test tube and the specimen in the barrel A is transferred into the test tube (not shown in the figures) at the push of the push shaft D and the piston C. The test tube is then placed in a centrifugal machine for specimen separation. After the specimen is separated into multiple layers inside the test tube, different layers of specimen solution (not shown in the figures) are extracted with a syringe to complete specimen collection.

The foregoing conventional specimen collection procedure is however rather complicated. In particular, after a blood specimen is extracted and stored in the barrel A, it needs to be transferred to a test tube. When blood needs to be transferred into another container, such as an injection syringe, a test tube or a dropper, during a specimen collection procedure, the risk of specimen contamination and the cost of specimen collection are greatly increased.

There have been attempts to improve the disadvantages of the foregoing specimen collection procedure, which primarily involve substituting the barrel A of the syringe for the test tube. That is, after the needle B is inserted into a human blood vessel and the push shaft D is pulled to extract a human blood specimen and store it in the barrel A, the needle B at a front end of the barrel A and the push shaft D at a rear end thereof are removed, and the front and rear ends of the barrel A are sealed (not shown in the figures). The barrel A storing the specimen may then be used as a test tube and placed in a centrifugal machine. After blood plasma is separated, the plugs sealing the front and rear ends of the barrel A are removed, the push shaft D is re-assembled, impurities like fat and water at a front segment of the barrel A are removed at the push of the push shaft D, and then the blood plasma at a middle segment of the barrel A is pushed into a test container. This improved specimen collection procedure is simple and requires fewer containers.

However, the foregoing improved procedure has the following disadvantage. The barrel A of a conventional injection syringe has a hanging portion A1 (as shown in FIG. 1) extending at a periphery surrounding a rear end opening of the barrel A to facilitate handling of the syringe and force application on the push shaft D. However, a barrel A with a hanging portion A1 may not be placed in a centrifugal machine unless being placed upside down with the front end of the barrel A at the bottom. As a result, the separated red blood cells are located at the front end of the barrel A (as shown in FIG. 2), while the blood plasma is located at the middle segment of the barrel A. When the push shaft D pushes the piston C, the blood plasma of a smaller volume may not easily push the red blood cells of a larger volume out of the barrel A, which causes the blood plasma to mix again with the red blood cells at the front end of the barrel A. It is in vain to separate blood plasma by a centrifugal machine if it may not be extracted.

To effectively solve the foregoing disadvantage, the present invention provides a specimen collector wherein red blood cells separated by a centrifugal machine are located at a rear end of the barrel A instead of at a front end thereof. In this manner, the blood plasma of a smaller volume may be pushed by the red blood cells of a larger volume out of the barrel A without causing undesirable re-mixture of the two.

SUMMARY OF THE INVENTION

It is a primary objective of the present invention to improve the foregoing disadvantage and provide a specimen collector wherein a needle is fitted to an end of a barrel, a specimen is extracted into the barrel with the coordination of the needle, a shaft body and a piston, the barrel is sealed up after the needle and the shaft body are removed with a first seal cap and a second seal cap respectively for subsequent centrifugal treatment of the specimen, and then the shaft body alone is re-assembled after the first and second seal caps are removed for the piston to be pushed by the shaft body to expel any (wanted or unwanted) specimen from the barrel. Further, in an interior of the foregoing barrel is disposed at least a piston stopper for stopping the piston from being accidentally pulled out of the barrel in prevention of contamination or infection as a result of specimen spillover.

It is a primary objective of the present invention to extract or expel an accurate volume of specimen with the help of a first graduated section and a second graduated section marked on the barrel.

To achieve the foregoing purpose, the present invention provides a multi-functional specimen collector, comprising: a barrel with a first graduated section and a second graduated section whose middle segment and rear end have a same outer diameter; a shaft body removably disposed in the barrel; a piston removably connected to an end of the shaft body and located in the barrel; a first seal cap removably connected to an end of the barrel; a second seal cap removably connected to the piston after the shaft body is removed; wherein at least a stopper is disposed at an opening inside the barrel whose middle segment and rear end have a same outer diameter for restricting a moving range of the piston inside the barrel to prevent the piston from being accidentally pulled out of the barrel and causing a specimen spillover. Further, on a surface of the barrel are marked a first graduated section and a second graduated section, the first graduated section having first marked parts and the second graduated section having second marked parts with marks in inverted sequence.

DETAILED DESCRIPTION OF THE PREFERRED EMBODIMENTS

Figure 1:
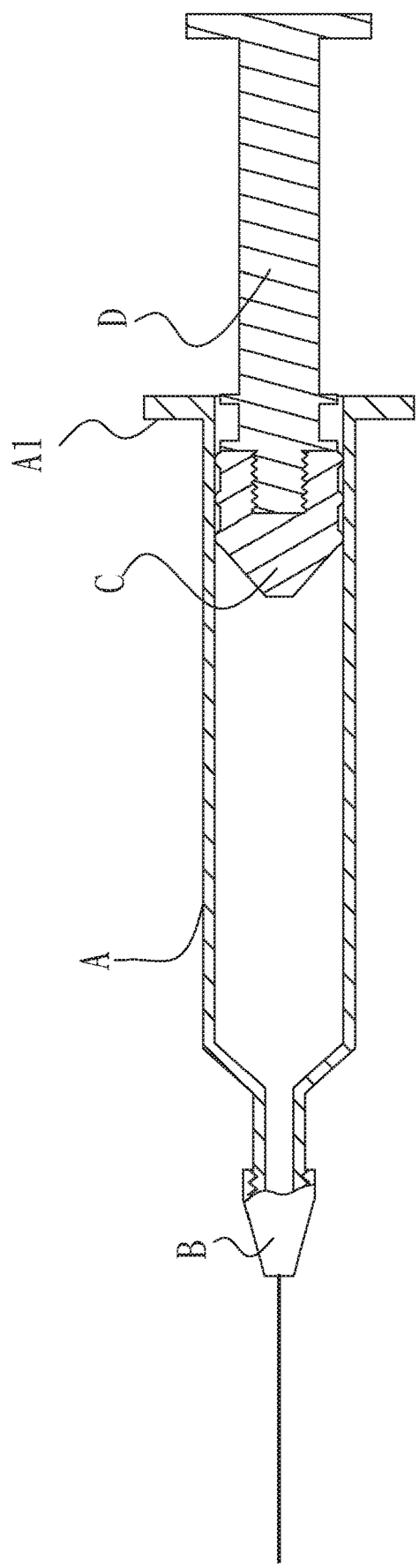
FIG. 1 is a schematic structural view of a conventional injection syringe.
Figure 2:
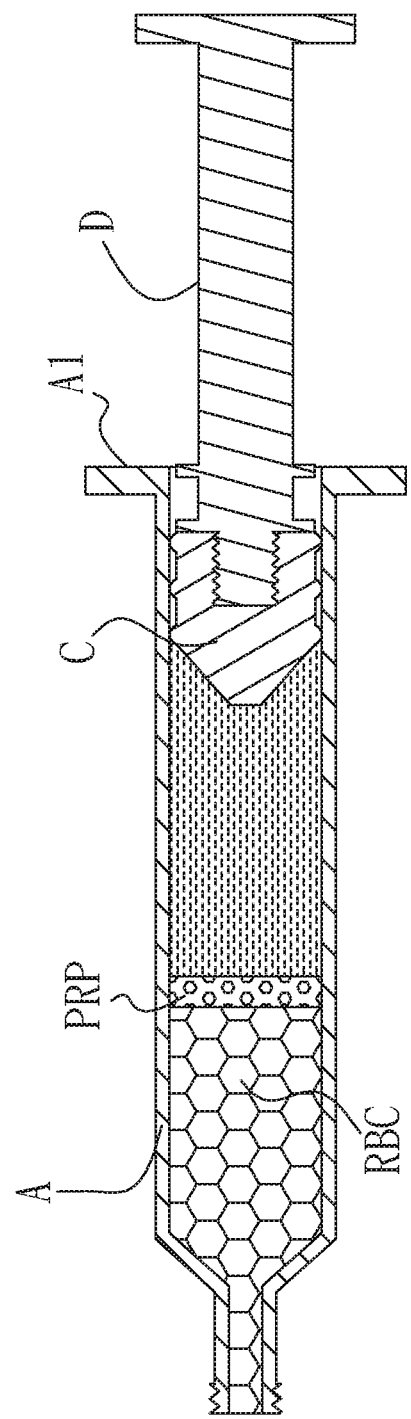
FIG. 2 is another schematic structural view of a conventional injection syringe.
Figure 3:
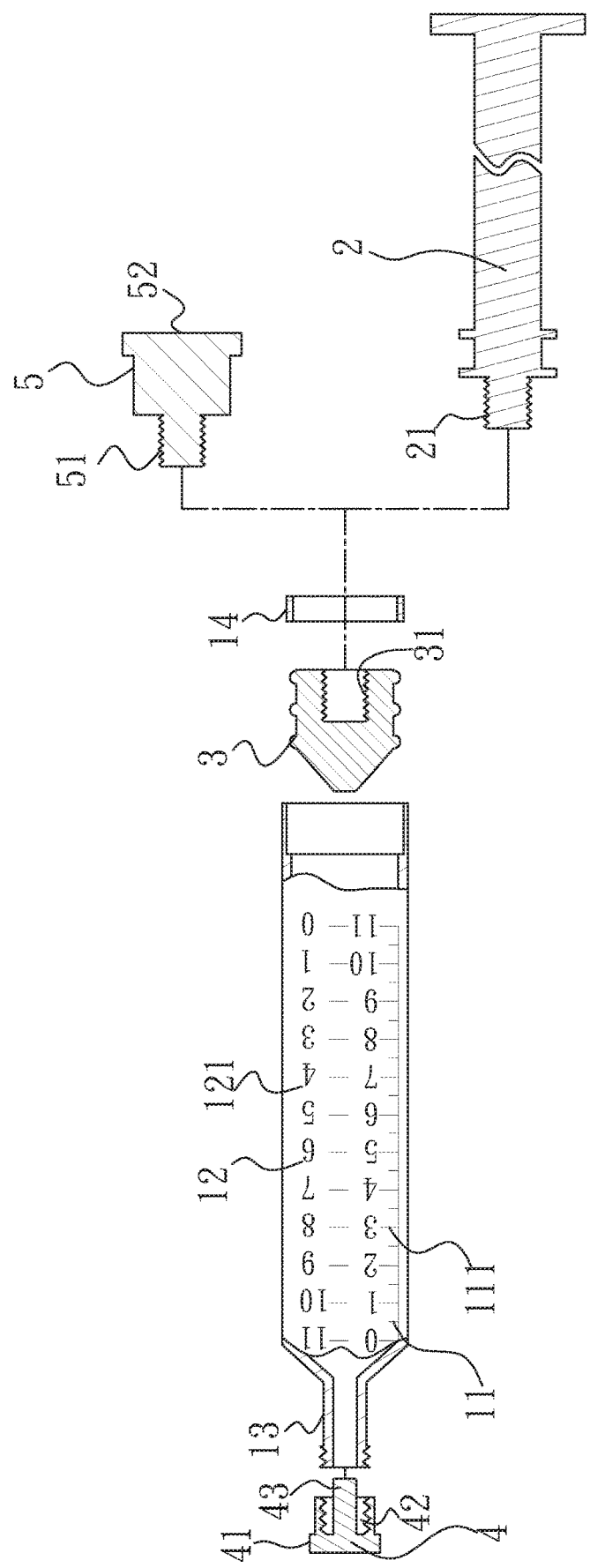
FIG. 3 is a schematic view of a basic structure according to the present invention.
Figure 4:
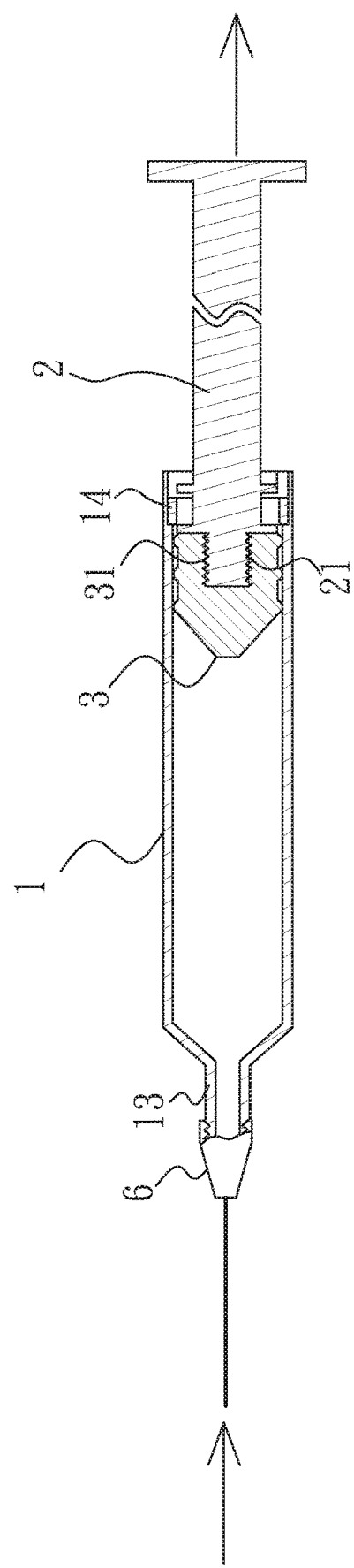
FIG. 4 is a first schematic view of a multi-functional specimen collector in use according to the present invention.

Please refer to FIGS. 3, 4, 5 and 6. As the figures show, the present invention provides a multi-functional specimen collector comprising at least a barrel 1, a shaft body 2, a piston 3, a first seal cap 4 and a second seal cap 5; the foregoing barrel 1 has a first graduated section 11 and a second graduated section 12 thereon, wherein the first graduated section 11 has a plurality of first marked parts 111 and the second graduated section 12 has a plurality of second marked parts 121 with marks in inverted sequence (as FIG. 4 shows); and at one end of the barrel 1 is disposed a threaded bush 13 and in an interior at another end of the barrel is disposed a stopper 14 for restricting a moving range of the piston inside the barrel to prevent the piston 3 from being accidentally pulled out of the barrel 1 and causing a specimen spillover. That is, the outer diameter of the stopper 14 and the inner diameter of the barrel 1 are designed to closely fit each other, the inner diameter of the stopper 14 needs to be smaller than the outer diameter of the piston 3 to prevent the piston 3 from being accidentally pulled out of the barrel 1, but the inner diameter of the stopper 14 needs to be larger than the largest outer diameter of the shaft body 2.

The shaft body 2 is removably disposed in the barrel 1, and at one end of the shaft body 2 is disposed a threaded rod 21. The piston 3 is removably connected to one end of the shaft body 2 and located in the barrel 1, and on the piston 3 is disposed an inner threaded hole 31 which is removably connected to the threaded rod 21 disposed on the shaft body 2.

The first seal cap 4 is removably connected to one end of the barrel 1, wherein the first seal cap 4 includes a turning knob 41, an inner threaded hole 42 disposed in the turning knob 41 and removably connected to the threaded bush 13, and an insert pin 43 disposed in the inner threaded hole 42 and screwed in the threaded bush 13.

The second seal cap 5 is removably connected to the piston 3 after the shaft body 2 is removed, wherein at one end of the second seal cap 5 is disposed a threaded rod 51 removably connected to the inner threaded hole 31 disposed in the piston 3 and at another end is disposed a turning knob 52. The outer shape of the foregoing first and second seal caps are designed to fit the base of a centrifugal machine, so that the barrel 1 may be steadily placed in a centrifugal machine for centrifugal treatment (not shown in the figures) whether the barrel 1 is placed with the first seal cap 4 or the second seal cap 5 at the bottom.

When the present invention is in use (e.g. for separating blood plasma), the needle 6 is connected to the threaded bush 13 of the barrel 1, and the threaded rod 21 of the shaft body 2 is connected to the inner threaded hole of the piston 3. The needle 6 may then be inserted into a human blood vessel, and the shaft body 2 is pulled for extracting blood into the barrel 1 with the coordination of the shaft body 2 and the piston 3. During extraction the volume of the extracted blood is shown by the first marked parts 111 of the first graduated section 11, and the stopper 14 may prevent the piston 3 from being pulled out of the barrel 1 by misapplied force.

After extraction the needle 6 and the shaft body 2 are respectively removed from the threaded bush 13 of the barrel 1 and the inner threaded hole 31 of the piston 3. The inner threaded hole 42 of the first seal cap 4 is aligned with the threaded bush 13 of the barrel 1, and a turning force is applied on the turning knob 41 to connect the inner threaded hole 42 and the threaded bush 13. The insert pin 43 is screwed in the threaded bush 13, then the threaded rod 51 of the second seal cap 5 is aligned with the inner threaded hole 31 of the piston 3, and a turning force is applied on the turning knob 52 to connect the threaded rod 51 and the inner threaded hole 31. In this manner, the barrel 1 is sealed by the first seal cap 4 and the second seal cap 5 and the extracted blood specimen is stored in the barrel 1.

Figure 5:
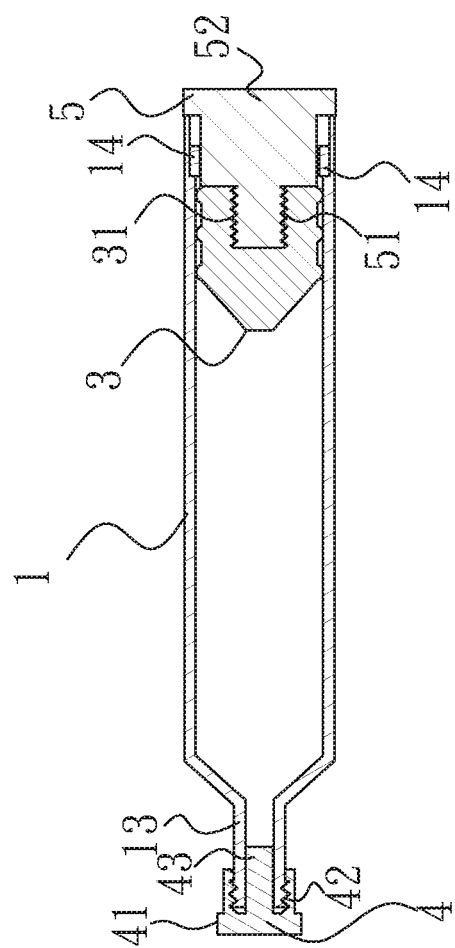
FIG. 5 is a second schematic view of a multi-functional specimen collector in use according to the present invention.
Figure 6:
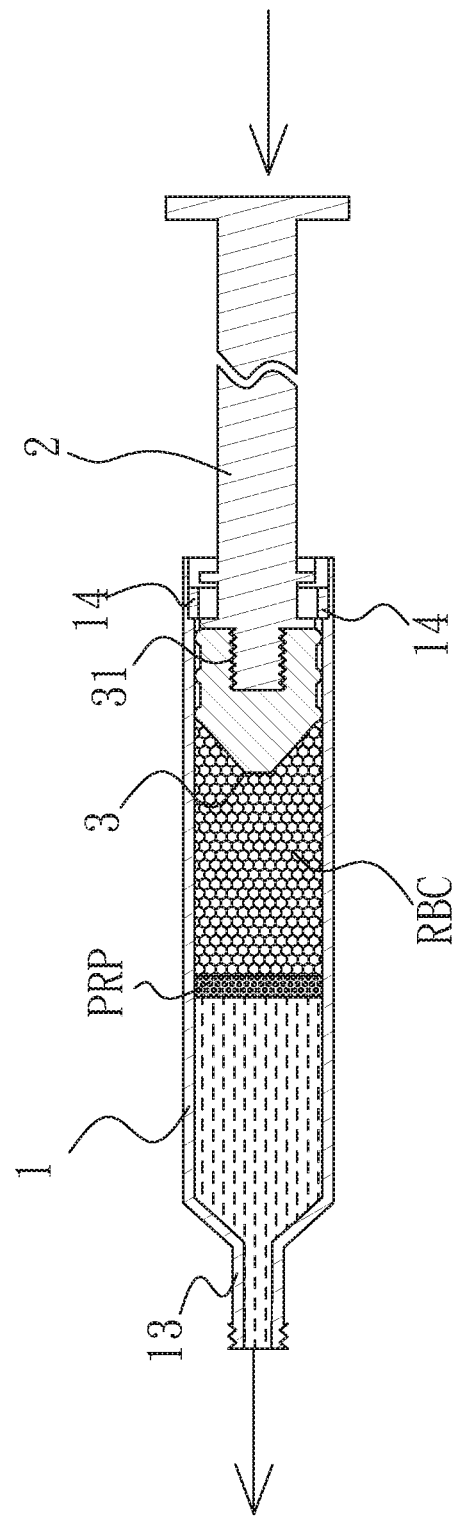
FIG. 6 is a third schematic view of a multi-functional specimen collector in use according to the present invention.

After the barrel 1 is sealed by the first seal cap 4 and the second seal cap 5, the barrel 1 storing the extracted blood specimen may be directly placed in a centrifugal machine for high-speed centrifugal treatment to separate blood plasma (as FIG. 5 shows). After separation treatment is complete, the second seal cap 5 is first removed from the piston 3, the shaft body 2 is re-assembled, and then the first seal cap 4 is removed from the threaded bush 13. The shaft body 2 may then be pushed to expel the blood plasma from the threaded bush 13 at one end of the barrel 1 with the piston 3. During expulsion the volume of the expelled blood plasma is shown by the second marked parts 121 of the second graduated section 12 (as FIGS. 3 and 6 show).

In view of the foregoing, a multi-functional specimen collector according to the present invention may effectively improve the disadvantage of conventional specimen collectors. After a needle is connected to one end of the barrel, a specimen is extracted into the barrel with the coordination of the needle, shaft body and piston. After extraction the needle and the shaft body are removed, and the barrel is sealed with a first and a second seal caps for the subsequent specimen separation procedure. After separation is complete, the first and second seal caps are removed, and wanted or unwanted specimen materials are expelled from the barrel with the shaft body. During extraction or expulsion, the first and second graduated sections may help to extract or expel an exact volume of the specimen. A multi-functional specimen collector according to the present invention is easy to handle and may effectively prevent the specimen from contamination at a reduced cost.

What is claimed is:
1. A multi-functional specimen collector, comprising:
a barrel, at a front end thereof is disposed a threaded bush for connecting to a needle, a middle segment and a rear end thereof have a same outer diameter, at the rear end thereof is disposed a stopper, and on a surface thereof are marked a first graduated section and a second graduated section, with the first graduated section hav- ing first marked parts and the second graduated section having second marked parts with marks in inverted sequence;

a shaft body removably disposed in the barrel, thereon is disposed a first threaded rod removably connected to a piston;

the piston disposed in the barrel and removably connected to the first threaded rod disposed on the shaft body, thereon is disposed an inner threaded hole removably connected to the shaft body;

a first seal cap removably connected to the front end of the barrel for sealing, comprising a first turning knob, an inner threaded hole disposed in the first turning knob and removably connected to the threaded bush, and an insert pin disposed in the inner threaded hole and screwed in the threaded bush; and a second seal cap, at one end thereof is disposed a second threaded rod removably connected to the inner threaded hole disposed on the piston, and at another end thereof is disposed a second turning knob for connecting to the piston after the shaft body is removed to seal the rear segment of the barrel;

wherein the stopper is disposed at the rear end of the barrel, and an outer diameter of the stopper is larger than an inner diameter of the middle segment of the barrel and is smaller than the outer diameter of the barrel.

2. The multi-functional specimen collector of claim 1, wherein the inner diameter of the middle segment of the barrel is smaller than an inner diameter of the rear end of the barrel.

3. The multi-functional specimen collector of claim 2, wherein the outer diameter of the stopper closely fits the inner diameter of the rear end of the barrel.

4. The multi-functional specimen collector of claim 1, wherein an inner diameter of the stopper is smaller than an outer diameter of the piston.

5. The multi-functional specimen collector of claim 1, wherein an inner diameter of the stopper is larger than a largest outer diameter of the shaft body.

\* \* \* \* \*